US006641843B1

(12) United States Patent
Brooks

(10) Patent No.: US 6,641,843 B1
(45) Date of Patent: Nov. 4, 2003

(54) PHARMACEUTICAL COMPOSITIONS

(75) Inventor: Nikki Thoennes Brooks, Glen Allen, VA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/601,671

(22) PCT Filed: Feb. 4, 1999

(86) PCT No.: PCT/EP99/00663

§ 371 (c)(1),
(2), (4) Date: Aug. 4, 2000

(87) PCT Pub. No.: WO99/39691

PCT Pub. Date: Aug. 12, 1999

(30) Foreign Application Priority Data

Feb. 6, 1998  (GB) ............................................... 9802472

(51) Int. Cl.[7] ................................................. A61K 9/14
(52) U.S. Cl. ...................... 424/489; 424/439; 424/488; 514/261; 514/262; 514/264
(58) Field of Search ............................... 514/261, 262, 514/264; 424/422, 435, 9, 484, 488

(56) References Cited

U.S. PATENT DOCUMENTS

| 5,034,394 A | | 7/1991 | Daluge | ........................ 514/261 |
| 5,089,500 A | | 2/1992 | Daluge | ........................ 514/261 |
| 5,206,435 A | * | 4/1993 | Daluge | ........................... 564/1 |
| 5,567,703 A | | 10/1996 | Vince et al. | .................. 514/261 |
| 5,763,607 A | | 6/1998 | Vince et al. | .................. 544/277 |
| 5,922,694 A | | 7/1999 | Vince et al. | .................... 514/81 |
| 5,962,684 A | | 10/1999 | Vince et al. | ................. 544/254 |
| 6,072,053 A | | 6/2000 | Vince et al. | ................. 544/264 |
| 6,124,319 A | * | 9/2000 | MacCoss et al. | ........... 514/318 |
| 6,177,464 B1 | * | 1/2001 | Cuny et al. | .................. 514/530 |

FOREIGN PATENT DOCUMENTS

| EP | 0434450 A | 6/1991 |
| WO | WO 9606844 A | 3/1996 |
| WO | WO-97/49410 A1 * | 12/1997 |
| WO | WO 9852949 A | 11/1998 |

* cited by examiner

Primary Examiner—James M. Spear
Assistant Examiner—Liliana Di Nola-Baron
(74) Attorney, Agent, or Firm—Amy H. Fix

(57) ABSTRACT

The present invention relates to pharmaceutical compostions of (1S,4R)-cis-4-[2-amino-6-cyclopropylamino}-9H-purin-9-yl]-2-cyclopentene-1-methanol (1592U89).

14 Claims, No Drawings

PHARMACEUTICAL COMPOSITIONS

This application is filed pursuant to 35 U.S.C. §371 as a United States National Phase Application of International Application No. PCT/EP99/00663 filed Feb. 4, 1999, which claims priority from GB9802472.2 filed Feb. 6, 1998.

The present invention relates to novel pharmaceutical compositions of (1S,4R)-cis-4-[2-amino-6-cyclopropylamino)-9H-purin-9-yl]-2-cyclopentene-1-methanol.

(1S,4R)-cis-4-[2-amino-6-cyclopropylamino)-9H-purin-9-yl]-2-cyclopentene-1-methanol and its antiviral use, particularly against HIV infections is described in European Patent Specification Number 0434450. The succinate salt of (1S,4R)-cis-4-[2-amino-6-cyclopropylamino)-9H-purin-9-yl]-2-cyclopentene-1-methanol is described in WO96/06844. The hemisulfate salt of (1S,4R)-cis-4-[2-amino-6-cyclopropylamino)-9H-purin-9-yl]-2-cyclopentene-1-methanol is described in WO98/52949.

(1S,4R)-cis-4-[2-amino-6-cyclopropylamino)-9H-purin-9-yl]-2-cyclopentene-1-methanol (also known as 1592U89) is currently under clinical investigation as an anti-HIV pharmaceutical agent. There exists a need for the compound to be prepared in solution form, for example for pediatric use.

Solutions of (1S,4R)-cis-4-[2-amino-6-cyclopropylamino)-9H-purin-9-yl]-2-cyclopentene-1-methanol are bitter-tasting and therefore require the addition of sweeteners and taste-maskers. However, formulation of (1S,4R)-cis-4-[2-amino-6-cyclopropylamino)-9H-purin-9-yl]-2-cyclopentene-1-methanol in solution is difficult because materials containing a —COOH group present problems with (1S,4R)-cis-4-[2-amino-6-cyclopropylamino)-9H-purin-9-yl]-2-cyclopentene-1-methanol compatibility. For example, glucose forms an adduct with the compound by replacing the methanol group on the cyclopentyl ring of (1S,4R)-cis-4-[2-amino-6-cyclopropylamino)-9H-purin-9-yl]-2-cyclopentene-1-methanol. (1S,4R)-cis-4-[2-amino-6-cyclopropylamino)-9H-purin-9-yl]-2-cyclopentene-1-methanol has been found to be incompatible with sucrose (which degrades to glucose and fructose) as well as glucose.

Solutions of (1S,4R)-cis-4-[2-amino-6-cyclopropylamino)-9H-purin-9-yl]-2-cyclopentene-1-methanol containing sorbitol result in a color change and the formation of dark colored particulates at pH 4.5–6.5.

In addition, propylene glycol concentration appears to have an influence on color formation, with higher levels of propylene glycol (10%) causing color formation.

We have found that sorbitol or saccharin or a combination of sorbitol and saccharin are compatible with (1S,4R)-cis-4-[2-amino-6-cyclopropylamino)-9H-purin-9-yl]-2-cyclopentene-1-methanol and do not lead to the formation of adducts with it. In addition, lowering the pH to about 4.0 eliminates the color change and the formation of particulates. We have also found that combinations of fructose, acesulfame and saccharin are compatible with (1S,4R)-cis-4-[2-amino-6-cyclopropylamino)-9H-purin-9-yl]-2-cyclopentene-1-methanol. In addition, we have found that abacavir is stable in pH ranges of about 2.0 to about 4.5 and about 6.6 to 7.5. Advantageously, the pH may be 3.8 to 4.5. We have also found that the addition of a metal chelator, for example citrate, improves the stability of abacavir in solution.

According to a first aspect of the invention there is provided a pharmaceutical composition comprising (1S,4R)-cis-4-[2-amino-6-cyclopropylamino)-9H-purin-9-yl]-2-cyclopentene-1-methanol and sorbitol at a range of pH from about 2.0 to about 4.5, advantageously pH 4.0. In an alternative embodiment, there is provided a pharmaceutical composition comprising (1S,4R)-cis-4-[2-amino-6-cyclopropylamino)-9H-purin-9-yl]-2-cyclopentene-1-methanol and saccharin at a range of pH from about 2.0 to about 4.5, advantageously pH 4.1. The pharmaceutical composition may comprise both sorbitol and saccharin at a range of pH from about 2.0 to about 4.5, advantageously pH 4.1.

A further aspect of the invention includes compositions comprising (1S,4R)-cis-4-[2-amino-6-cyclopropylamino)-9H-purin-9-yl]-2-cyclopentene-1-methanol and sorbitol and/or saccharin at a pH range of about 6.6 to about 7.5, advantageously pH 7.0. Compositions at about pH 7 may include propylene glycol or other suitable solubilizer to improve solubility.

According to another aspect of the invention there is provided a pharmaceutical composition comprising (1S,4R)-cis-4-[2-amino-6-cyclopropylamino)-9H-purin-9-yl]-2-cyclopentene-1-methanol and a sweetening agent compatible with said (1S,4R)-cis-4-[2-amino-6-cyclopropylamino)-9H-purin-9-yl]-2-cyclopentene-1-methanol at a pH range of about 2.0 to about 4.5.

In a further aspect of the invention there is provided a pharmaceutical composition comprising (1S,4R)-cis-4-[2-amino-6-cyclopropylamino)-9H-purin-9-yl]-2-cyclopentene-1-methanol and fructose, acesulfame, and saccharin at a range of pH from about 2.0 to about 4.5, advantageously pH 4.0. Alternatively, the compositions may be formulated at a pH range of about 6.6 to 7.5, advantageously pH 7.0.

According to a further aspect of the present invention there is provided a pharmaceutical composition comprising (1S,4R)-cis-4-[2-amino-6-cyclopropylamino)-9H-purin-9-yl]-2-cyclopentene-1-methanol, sorbitol, saccharin and citrate at a range of pH from about 2.0 to about 4.5. The citrate ion concentration may advantageously be in the range of about 0.01M to about 0.13M. Advantageously, sodium citrate and citric acid may be used.

The compositions of the present invention may also comprise one or more pharmaceutically acceptable organic solvents, for example, propylene glycol, polypropylene glycol, polyethylene glycol, and the like; pharmaceutically acceptable alcohols, for example ethanol or 2-(2-ethoxyethoxy)ethanol and the like; antioxidants, for example, edetate disodium, malic acid, fumaric acid, or sodium metabisulfite, and the like; pharmaceutically acceptable acids, for example, hydrochloric acid, acetic acid, citric acid, sulfuric acid, and the like; and oils or surfactants, and the like.

The compositions of the present invention may also comprise other pharmaceutically acceptable sweetening agents and/or flavoring agents, for example, aspartame, sucralose, and the like and/or cherry flavor, artificial banana flavor, caramel, chocolate mint flavor, grape flavor, wild cherry flavor, raspberry flavor, strawberry flavor, citrus flavor, orange flavor, pineapple flavor, citrus lime flavor, citrus cream flavor, cherry vanilla flavor, creme de menthe flavor and the like.

According to the present invention, any ester of hydroxybenzoate (parabens) or combination of such esters may be used, including methyl and propyl paraben and butyl and propyl paraben combinations. Sodium benzoate (0.02–0.5% w/v) or potassium sorbate (0.05–0.2% w/v) may be used as preservatives.

In a further aspect of the present invention, there is provided (1S,4R)-cis-4-[2-amino-6-cyclopropylamino)-9H- purin-9-yl]-2-cyclopentene-1-methanol compositions containing methyl paraben and propyl paraben. For oral solutions and suspensions, the range of methyl paraben concentration may be 0.15–0.2% (1.5 mg/mL to 2 mg/mL) and the range of propyl paraben concentration may be 0.01% to 0.02% (0.1 to 0.2 mg/mL).

According to a further aspect of the present invention, any suitable buffer may be used to provide a pH>5.5. Advantageously, sodium citrate or phosphate may be used. To achieve a pH range of about 2.0 to about 4.5, advantageously citrate, fumarate, glutarate, malate, maleate, tartrate or acetate may be used.

Included in the invention are the pharmaceutically acceptable salts, esters, or salts of such esters of (1S,4R)-cis-4-[2-amino-6-cyclopropylamino)-9H-purin-9-yl]-2-cyclopentene-1-methanol, or any other compound which, upon administration of a safe and therapeutically effective amount of the compound to a human subject, is capable of providing (directly or indirectly) the antivirally active metabolite or residue thereof.

Preferred esters in accordance with the invention are independently selected from the following group: (1) carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$ alkyl, or $C_{1-4}$ alkoxy), or amino; (2) sulphonate esters, such as alkyl- or aralkylsulphonyl (for example, methanesulphonyl); (3) amino acid esters (for example, L-valyl or L-isoleucyl); and (4) phosphonate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group. Any reference to any of the above compounds also includes a reference to a physiologically acceptable salt thereof.

Preferred derivatives of 1592U89 are the mono-, di-, and tri-phosphate esters of (1R, 4S)-9-[4-(hydroxymethyl)-2-cyclopenten-1-yl]guanine (carbovir).

Examples of physiologically acceptable salts of 1592U89 and their physiologically acceptable derivatives include salts derived from an appropriate base, such as an alkali metal (for example, sodium), an alkaline earth (for example, magnesium), ammonium and $NX_4^+$ (wherein X is $C_{1-4}$ alkyl). Physiologically acceptable salts of an hydrogen atom or an amino group include salts of organic carboxylic acids such as acetic, lactic, tartaric, malic, isethionic, lactobionic, and succinic acids, organic sulphonic acids, such as methanesulphonic, ethanesulphonic, benzenesulphonic and p-toluenesulphonic acids and inorganic acids, such as hydrochloric, sulphuric, phosphoric and sulphamic acids. Physiologically acceptable salts of a compound of an hydroxy group include the anion of said compound in combination with a suitable cation such as $Na^+$, $NH_4^+$ and $NX_4^+$ (wherein X is a $C_{1-4}$ alkyl group).

For therapeutic use, salts of 1592U89 will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived from a physiologically acceptable acid or base, are within the scope of the present invention.

Preferred salts of 1592U89 are the succinate salt and the hemisulfate salt.

The formulations according to the invention may be presented in various forms adapted for direct oral administration including liquid forms, for example, syrups, suspensions, or solutions. The formulations, according to the invention, may include other pharmaceutically acceptable carriers as excipients conventionally used in such formulations.

The compositions of the present invention may be formulated using methods and techniques suitable for the compositions' physical and chemical characteristics and that are commonly employed by persons skilled in the art of preparing oral dosage forms (Remington, *The Science and Practice of Pharmacy,* 19th ed., 1995).

The compositions according to the invention may be employed in medical therapy in combination with other therapeutic agents suitable in the treatment of HIV infections, such as nucleoside reverse transcriptase inhibitors for example zidovudine, zalcitabine, didanosine, stavudine, 5-chloro-2',3'-dideoxy-3'-fluorouridine, lamivudine, and (2R,5S)-5-fluoro-1-[2-(hydroxymethyl)1,3-oxathiolan-5-yl]cytosine; non-nucleoside reverse transcriptase inhibitors for example HEPT, TIBO derivatives, atevirdine, L-ofloxacin, L-697,639, L-697-661, nevirapine (BI-RG-587), loviride (α-APA), delavuridine (BHAP), phosphonoformic acid, (−)-6-chloro-4-cyclopropylethynyl-4-trifluoromethyl-1,4-dihydro-2H-3,1-benzoxazin-2-one (L-743,726 or DMP-266), and isopropyl (2S)-7-fluoro-3,4-dihydro-2-ethyl-3-oxo-1-(2H)-qinoxalinecarboxylate (HBY 1293); HIV protease inhibitors for example saquinavir, indinavir, ritonavir, nelfinavir, and 141W94; other anti-HIV agents for example soluble CD4; immune modulators for example interleukin II, erythropoetin, tucaresol; and interferons for example α-interferon.

According to another aspect, the present invention provides a method for the treatment of an HIV infection in an infected animal, for example, a mammal including a human, which comprises treating said animal with a composition according to the invention.

Reference herein to treatment extends to prophylaxis as well as the treatment of established infections, symptoms, and associated clinical conditions such as AIDS related complex (ARC), Kaposi's sarcoma, and AIDS dementia.

The present invention also provides the use of a composition, as hereinbefore described, in the manufacture of a medicament for the treatment and/or prophylaxis of HIV infections and associated clinical conditions hereinbefore described.

In general a suitable dose of 1592U89 for administration to a human for treatment of an HIV injection may be in the range of 0.1 to 120 mg per kilogram body weight of the recipient per day, preferably in the range of 3 to 90 mg per kilogram body weight per day and most preferably in the range 5 to 60 mg per kilogram body weight per day.

Unless otherwise indicated all weights of active ingredients are calculated in terms of the drug per se. In the case of a physiologically functional derivative of 1592U89 or a solvate of any thereof the figures would be increased proportionately. The desired dose may preferably be presented as one, two, three, four, five, six or more sub-doses administered at appropriate intervals throughout the day. These sub-doses may be administered in unit dosage forms, for example, containing from 1 to 1500 mg, preferably from 5 to 1000 mg, most preferably from 10 to 700 mg of active ingredient per unit dosage form. Alternatively, if the condition of the recipient so requires, the dose may be administered as a continuous infusion.

Pharmaceutical compositions according to the present invention may contain one or more pharmaceutically acceptable carriers or excipients and optionally other therapeutic agents. The carrier(s) must be acceptable in the sense of being compatible with the other ingredients of the formula and not deleterious to the recipient thereof.

The present invention may conveniently be presented as a pharmaceutical composition in a unit dosage form. A convenient unit dosage composition contains the active ingredients in amounts of from 50 mg to 3 g each, for example, 100 mg to 2 g.

The concentration of 1592U89 hemisulfate salt may be 1–90 mg/ml at a pH range of about 2.0 to about 4.5.

The unit dosage form may be prepared by any methods well known in the art of pharmacy. Such methods represent a further feature of the present invention and include the step of bringing into association the active ingredients with the carrier which constitutes one or more accessory ingredients. In general, the compositions are prepared by uniformly and intimately bringing into association the active ingredients with liquid carriers or finely divided solid carriers or both, and then if necessary shaping the product Preferred unit dosage compositions are those containing a daily dose or daily subdose of the active ingredients, as hereinbefore recited, or an appropriate fraction thereof.

Pharmaceutical compositions are often prescribed to the patient in "patient packs" containing the whole course of treatment in a single package, usually a blister pack or a foil pouch. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physicians instructions and, therefore, lead generally to more successful treatment.

It should be understood that in addition to the ingredients particularly mentioned above the compositions of this invention may include other agents conventional in the art, for example, those suitable for oral administration may include such further agents as sweeteners, thickeners and flavoring agents.

1592U89 may be prepared by the method described in European Patent Specification Number 0434450 or PCT Application No. GB95/00225 which are incorporated herein by reference hereto.

The succinate salt of 1592U89 may be prepared by the method described in PCT Application No. GB95/02014, which is incorporated herein by reference hereto.

The following examples are intended for illustration only and are not intended to limit the scope of the invention in any way.

EXAMPLE 1

Preparation of (1S,4R)-cis-4-[2-Amino-6-cyclopropylamino)-9H-purin-9-yl]-2-cyclopentene-1-methanol hemisulfate salt A stirred mixture of water (25 ml) and isopropanol (IPA) (100 ml) was heated to 45 to 55° C. and (1S,4R)-cis-4-[2-amino-6-cyclopropylamino)-9H-purin-9-yl]-2-cyclopentene-1-methanol succinate salt (WO 96/06844) (50 g)) was added, and washed in with IPA (12.5 ml). The mixture was heated under reflux for about 0.5 h to give a clear solution and then cooled to 65 to 75° C. and a solution of concentrated sulfuric acid (6.07 g) in water (12.5 ml) was added. A mixture of IPA (37.5 ml) and water (12.5 ml) was added and the solution was cooled to 45 to 55° C., whereupon a seed of authentic (1S,4R)-cis-4-[2-amino-6-cyclopropylamino)-9H-purin-9-yl]-2-cyclopentene-1-methanol hemisulfate salt was added. After stirring in this temperature range for about 1 h to allow crystallisation to become established, further IPA (300 mL) was added, maintaining the temperature of the mixture in the range 45 to 55° C. The suspension was cooled to 0 to 5° C. over about 2 h, and the product was filtered, washed with IPA (2×75 ml), and dried in vacuo at 40 to 45° C. to give the title compound as a fawn colored powder (34.3 g, 90%); m.p. 224–225° C. (decomp.); 1H-NMR (DMSO-d6) δ: 10.76(br m, 1, purine NH), 8.53(vbr m, 1, NH), 7.80(s,1,purine CH), 6.67(br m, 1, NH2), 6.13(m,1, =CH), 5.87(m,1,=CH), 5.40(m,1,NCH), 3.45(d, J=5.8 HZ,2, OCH2), 2.96(br, m, 1 CH of cyclopropyl), 2.87(m, 1, CH), 2.67–2.57 (M, 1, CH), 1.65–1.55(m, 1, CH), 0.84–0.64(m, 4, 2×CH2 of cyclopropyl).

EXAMPLE 2

(1S,4R)-cis-4-[2-Amino-6-cyclopropylamino)-9H-purin-9-yl]-2-cyclopentene-1-methanol (1592U89 Hemisulfate) oral solution A. Composition A

| Component | Grade (USP/NF) | Quantity/ Dosage Unit | Function |
|---|---|---|---|
| 1592U89 Hemisulfate | | 23.4[1] | Active |
| Sorbitol[2,3] | NF | 344.4 | Sweetener |
| Saccharin Sodium[3] | USP | 0.3 | Sweetener |
| Artificial Strawberry Flavor[3] | | 2.0 | Flavor |
| Artificial Banana Flavor[3] | | 2.0 | Flavor |
| Sodium Citrate (Dihydrate) | USP | 10.0 | pH Adjustment |
| Citric Acid (Anhydrous) | USP | 7.0 | pH Adjustment |
| Methylparaben | NF | 1.5 | Preservative |
| Propylparaben | NF | 0.18 | Preservative |
| Propylene Glycol | USP | 50.0 | Solubility Enhancer |
| Diluted Hydrochloric Acid/ Solution of Sodium Hydroxide | NF | to pH 4.0[5] | pH Adjustment |
| Purified Water[4] | USP | to 1.0 mL | Vehicle |

Notes:
[1]Hemisulfate salt converted to base using factor of 1.17, may be adjusted for purity.
[2]Sorbitol Solution USP or Noncrystallizing Sorbitol Solution NF may be substituted for Sorbitol NF.
[3]Quantity may vary ± 10% from that listed.
[4]Water for injection USP may be used in place of Purified Water USP throughout the manufacturing process.
[5]The pH may range from 3.8–4.5.

B. Preparation

500 L Batch Size, 20 mg (1S,4R)-cis-4-[2-amino-6-cyclopropylamino)-9H-purin-9 -yl]-2-cyclopentene-1-methanol per mL 1. Use of Sorbitol Solution 40% of the Propylene Glycol USP was added to an appropriately-sized auxiliary vessel. Methylparaben NF and Propylparaben NF was added to the Propylene Glycol USP with mixing, and mixed until dissolved. Purified Water USP was dispensed into a stainless steel manufacturing tank equipped with a suitable mixer to approximately 40% of final batch volume. The appropriate volume of Sorbitol Solution USP was dispensed into the manufacturing tank. While mixing, the 1592U89 Hemisulfate was added and mixed until dissolved. While continuing to mix, the paraben/ glycol solution, the remaining Propylene Glycol USP, artificial strawberry flavor, artificial banana flavor, Saccharin Sodium NF, Citric Acid Anhydrous USP, and Sodium Citrate Dihydrate USP were added and mixed until dissolved. The mixer was turned off and the solution brought to a volume of 500 L and mixed until a homogeneous solution was achieved. The solution was sampled and the pH measured. The pH was adjusted to 3.8–4.5 with NaOH or HCl solution. The final solution was filtered through a clarifying filter into an appropriately-sized receiving vessel. Clean, compressed, filtered air was blown into bottles and the bottles were filled with 1592U89 hemisulfate oral solution, capped, and torqued. Alternatively, Water for Injection USP may be used in place of Purified Water USP throughout the manufacturing procedure.

2. Use of Sorbitol NF

Alternatively, Sorbitol NF may be used in place of Sorbitol Solution USP. Purified Water USP was added to a volume of approximately 70% of the batch in a stainless steel manufacturing tank equipped with a suitable mixer. While mixing, the Sorbitol NF was mixed until dissolved. While mixing, the 1592U89 Hemisulfate was added and mixed until dissolved. While continuing to mix, the paraben/ glycol solution, the remaining Propylene Glycol USP, artificial strawberry flavor, artificial banana flavor, Saccharin Sodium NF, Citric Acid Anhydrous USP, and Sodium Citrate Dihydrate USP were added and mixed until dissolved. The mixer was turned off and the solution brought to a volume of 500 L and mixed until a homogeneous solution was achieved. The solution was sampled and the pH measured. The pH was adjusted to 4.0 with NaOH/HCl solution. The final solution was filtered through a clarifying filter into an appropriately-sized receiving vessel. Clean, compressed, filtered air was blown into bottles and the bottles were filled with 1592U89 hemisulfate oral solution, capped, and torqued.

EXAMPLE 3

(1S,4R)-cis-4-[2-Amino-6-cyclopropylamino)-9H-purin-9-yl]-2-cyclopentene-1-methanol (1592U89 Hemisulfate) oral solution A. Composition B

| Component | Quantity/Dosage Unit (mg/mL) |
|---|---|
| 1592U89 Hemisulfate | 23.4[1] |
| Fructose | 200.0 |
| Saccharin Sodium | 1.0 |
| Acesulfame K | 5.0 |
| Artificial Strawberry Flavor | 2.0 |
| Artificial Banana Flavor | 2.0 |
| Sodium Citrate (Dihydrate) | 10.0 |
| Citric Acid (Anhydrous) | 7.0 |
| Methylparaben | 1.5 |
| Propylparaben | 0.18 |
| Propylene Glycol | 50.0 |
| Diluted Hydrochloric Acid and/or solution of Sodium Hydroxide[4] | to pH 4.0 |
| Purified Water | to 1.0 mL |

[1]Hemisulfate salt converted to base using factor of 1.17, may be corrected for purity.

B. Preparation

40% of the Propylene Glycol USP was added to an appropriately-sized auxiliary vessel. Methylparaben NF and Propylparaben NF was added to the Propylene Glycol USP with mixing, and mixed until dissolved. Purified Water USP was added to a volume of approximately 70% of the batch in a stainless steel manufacturing tank equipped with a suitable mixer. While mixing, the Fructose USP was mixed until dissolved. While mixing, the 1592U89 Hemisulfate was added and mixed until dissolved. While continuing to mix, the paraben/glycol solution, the remaining Propylene Glycol USP, artificial strawberry flavor, artificial banana flavor, Saccharin Sodium NF, acesulfame, Citric Acid Anhydrous USP, and Sodium Citrate Dihydrate USP were added and mixed until dissolved. The mixer was turned off and the solution brought o a volume of 500 L and mixed until a homogeneous solution was achieved. The solution was sampled and the pH measured. The pH was adjusted to 3.8–4.5 with NaOH or HCl solution. The final solution was filtered through a clarifying filter into an appropriately-sized receiving vessel. Clean, compressed, filtered air was blown into bottles and the bottles were filled with 1592U89 hemisulfate oral solution, capped, and torqued.

Alternatively, Water for Injection USP may be used in place of Purified Water USP throughout the manufacturing procedure.

EXAMPLE 4

Preparation of (1S,4R)-cis-4-[2-amino-6-(cyclopropylamino)-9H-purin-9-yl]-2-cyclopentene-1-methanol (1S,4R)-cis-4-[2-amino-6-chloro-9H-purin-9-yl]-2-cyclopentene-1-methanol hydrochloride salt (EP0434450 (80 g)) was heated under reflux in industrial methylated spirits (IMS, 800 ml) with cyclopropylamine (110 ml) for about 5 h. The mixture was cooled to 70 to 75° C. and an aqueous solution of sodium hydroxide (10M, 55 ml, 2 molar equivalents) was added dropwise. The resultant suspension was cooled to 20 to 25° C. and filtered, the collected solids being washed with IMS (2×60 ml). The combined filtrates and washings were treated with charcoal (8 g) and the filter-aid Harborlite J2 (4 g) then heated to 40 to 50° C. After about 0.5 h, the mixture was cooled to 15 to 20° C. and the solids were removed by filtration, washed with IMS (2×60 ml and 1×80 ml) and the combined filtrates and washings were concentrated by distillation under reduced pressure to a residual volume of about 240 ml. IMS (560 ml) was added and the mixture was concentrated under reduced pressure to a residual volume of about 240 ml. The dilution and reconcentration was repeated and the resultant concentrate was diluted with IMS (240 ml) and heated to obtain a complete solution which was divided into four equal portions.

One portion was concentrated by distillation under reduced pressure to a residual volume of about 60 ml. Acetone (140 ml) was added and the mixture re-concentrated to about 60 ml. This dilution and re-concentration was repeated twice to give a fluid volume of about 80 ml. The resultant suspension was cooled to 0 to 5° C. and the product was filtered, washed with cold (0 to 5° C.) acetone (2×40 ml) and dried in vacuo to give the title compound as an orange solid (16.8 g, 90%); $^1$H-NMR (D$_2$O) δ: 7.71(s, 1, purine CH), 6.22(m, 1, =CH), 5.93(m, 1, =CH), 5.37(m, 1, NCH), 3.61(m, 2, OCH$_2$), 3.04(br m, 1, CH of cyclopropyl), 2.82(br m, 1,CH), 2.80–2.70(m, 1, CH), 1.58–1.50(m, 1, CH), 0.90–0.60(m, 4, 2×CH$_2$ of cyclopropyl).

EXAMPLE 5

Preparation of (1S,4R)-cis-4-[2-amino-6-(cyclopropylamino)-9H-purin-9-yl]-2-cyclopentene-1-methanol hemisulfate salt A stirred mixture of water (25 ml) and IPA (100 ml) was heated to 45 to 55° C. and (1S,4R)-cis-4-[2-amino-6-

(cyclopropylamino)-9H-purin-9-yl]-2-cyclopentene-1-methanol succinate salt (WO96/06844 (50 g)) was added, and washed in with IPA (12.5 ml). The mixture was heated under reflux for about 0.5 h to give a clear solution and then cooled to 65 to 75° C. and a solution of concentrated sulfuric acid (6.07 g) in water (12.5 ml) was added. A mixture of IPA (37.5 ml) and water (12.5 ml) was added and the solution was cooled to 45 to 55° C., whereupon a seed of authentic (1S,4R)-cis-4-[2-amino-6-(cyclopropylamino)-9H-purin-9-yl]-2-cyclopentene-1-methanol hemisulfate salt was added. After stirring in this temperature range for about 1 h to allow crystallisation to become established, further IPA (300 ml) was added, maintaining the temperature of the mixture in the range 45 to 55° C. The suspension was cooled to 0 to 5° C. over about 2 h, and the product was filtered, washed with IPA (2×75 ml), and dried in vacuo at 40 to 45° C. to give the title compound as a fawn coloured powder (34.3 g, 90%); m.p. 224–225° C. (decomp.); $^1$H-NMR (DMSO-d6) δ: 10.76 (br m, 1, purine NH), 8.53(vbr m, 1, NH), 7.80(s, 1, purine CH), 6.67(br m, 1, NH$_2$), 6.13(m, 1, =CH), 5.87(m, 1, =CH), 5.40(m, 1, NCH), 3.45(d, J=5.8 Hz, 2, OCH$_2$), 2.96(br m, 1, CH of cyclopropyl), 2.87(m, 1, CH), 267–2.57 (m, 1, CH), 1.65–1.55(m, 1, CH), 0.84–0.64(m, 4, 2×CH$_2$ of cyclopropyl).

EXAMPLE 6

Preparation of (1S,4R)-cis-4-[2-amino-6-(cyclopropylamino)-9H-purin-9-yl]-2-cyclopentene-1-methanol hemisulfate salt A stirred suspension of (1S,4R-cis-4-[2-amino-6-(cyclopropylamino)-9H-purin-9-yl]-2-cyclopentene-1-methanol succinate salt (WO96/06844 (1000 g)) in industrial methylated spirit (IMS) (7000 ml) was heated under reflux for about 0.5 h to obtain a clear solution. The solution was cooled to about 70° C. and a solution of concentrated sulfuric acid (121 g) in IMS (1000 ml) was added. After seeding with authentic (1S,4R-cis-4-[2-amino-6-(cyclopropylamino)-9H-purin-9-yl]-2-cyclopentene-1-methanol hemisulfate salt, the mixture was stirred at about 70° C. to allow the product to crystallise. After about 0.5 h, the mixture was cooled to 20 to 30° C. over about 2 h. The mixture was filtered, the cake was washed with IMS (2×2000 ml) and dried in vacuo at 40 to 45° C. to give the title compound as a fawn coloured powder (764 g, 92%), spectra identical to those of the product of Example 5.

EXAMPLE 7

Preparation of (1S,4R)-cis-4-[2-amino-6-(cyclopropylamino)-9H-purin-9-yl]-2-cyclopentene-1-methanol hemisulfate salt A suspension of (1S,4R)-cis-4-[2-amino-6-(cyclopropylamino)-9H-purin-9-yl]-2-cyclopentene-1-methanol succinate salt (10 g) in industrial methylated spirit (IMS) (30 ml) and water (5 ml) was heated under reflux for about 0.5 h to give a clear solution. The solution was cooled to 55 to 65° C. and a solution of concentrated sulfuric acid (1.21 g) in water (2.5 ml) was added, followed by a mixture of IMS (7.5 ml) and water (2.5 ml). The solution was further cooled to 45 to 55° C. and acetone (80 ml) was added over about 0.25 h to the mixture within this temperature range. The resultant suspension was cooled to 0 to 5° C. over about 1 h. The product was filtered, washed with acetone (2×10 ml) and dried in vacuo at 40 to 45° C. to give the title compound as a fawn coloured powder (6.28 g, 82%) which was spectroscopically identical to the product of Example 5.

EXAMPLE 8

Preparation of (1S,4R)-cis-4-[2-amino-6-(cyclopropylamino)-9H-purin-9-yl]-2-cyclopentene-1-methanol hemisulfate salt (1S,4R)-cis-4-[2-amino-6-(cyclopropylamino)-9H-purin-9-yl]-2-cyclopentene-1-methanol (Intermediate 1) (5.98 g) was suspended in IMS (40 ml) and the suspension was heated under reflux for about 0.5 h. The mixture was cooled to 70 to 75° C. and a mixture of a solution of concentrated sulfuric acid in IMS (10M, 1.03 ml, 0.5 molar equivalent) and IMS (10 ml) was added dropwise. The acid was washed in with further IMS (10 ml) and the resultant suspension was cooled to 0 to 5° C. The product was isolated by filtration, washed with IMS (2×12 ml) and dried in vacuo at 40 to 45° C. to yield the title compound as a pale yellow solid (6.15 g, 88%), spectra identical to those of the product of Example 5.

EXAMPLE 9

Preparation of (1S,4R)-cis-4-[2-amino-6-(cyclopropylamino)-9H-purin-9-yl]-2-cyclopentene-1-methanol hemisulfate salt A further portion of the IMS solution of Intermediate 1 was heated to 75 to 80° C. to ensure complete solution. This was cooled to 70 to 75° C. and a solution of concentrated sulfuric acid (3.90 g) in IMS (30 ml) was added dropwise, to give an orange coloured suspension. The mixture was cooled to 0 to 5° C. over about 2 h and the product was filtered, washed with IMS (2×40 ml) and dried in vacuo at 40 to 45° C. to give the title compound as a yellow/orange solid (17.7 g, 76%), spectra identical to those of the product of Example 5.

Of this product, 5.0 g was suspended in a mixture of isopropanol (IPA) (40 ml) and water (10 ml) and heated under reflux for about 0.5 h and then allowed to cool to 55 to 60° C., whereupon seeds of authentic (1S,4R)-cis-4-[2-amino-6-(cyclopropylamino)-9H-purin-9-yl]-2-cyclopentene-1-methanol hemisulfate salt were added. The suspension was cooled further to 0 to 5° C. and the temperature was maintained for about 1 h. The solid was filtered, washed with IPA (2×5 ml) and dried in vacuo at 40 to 45° C. to yield the title compound as a buff coloured powder (4.4 g, 88%), spectra identical to those of the product of Example 5.

EXAMPLE 10

(1S,4R)-cis-4-[2-amino-6-(cyclopropylamino)-9H-purin-9-yl]-2-cyclopentene-1-methanol benzoate salt (1S,4R)-cis-4-[2-amino-6-chloro-9H-purin-9-yl]-2-cyclopentene-1-methanol hydrochloride salt EP0434450 (70 g) was heated under reflux in IMS (700 ml) with cyclopropylamine (94.5 ml) for about 4 h. The solution was cooled to 45 to 50° C. and treated with filter-aid Harborlite J2 (3.5 g) and charcoal (7 g). After about 0.5 h, the mixture was cooled to 20 to 25° C. and filtered. The solids were washed with IMS (2×140 ml) and the combined filtrates and washings were concentrated by distillation under reduced pressure to a volume of about 210 ml. After dilution with IMS, (490 ml) the solution was re-concentrated to about 210 ml. The dilution and reconcentration was repeated once and the final concentrate was divided into seven equal portions. One portion was diluted with IMS (80 ml) and warmed until a complete solution was obtained. Benzoic acid (4.85 g) was added as a single portion and the mixture was heated at 70 to 75° C. to give a complete solution, which was then allowed to cool slowly. At 40 to 45° C. the mixture was seeded with authentic (1S,4R)-cis-4-[2-amino-6-(cyclopropylamino)-9H-purin-9-yl]-2-cyclopentene-1-methanol benzoate salt and the mixture was further cooled to 0 to 5° C. The solid was filtered, washed with IMS (2×20 ml) and dried in vacuo at 40 to 45° C. to give the title compound as a white solid (8.7 g, 64%), mpt: 156–157° C.; $^1$H-NMR (DMSO-d$_6$) δ: 7.95(m, 2, benzoate CH), 7.63(m, 1, benzoate CH), 7.61(s, 1, purine CH), 7.50(m, 2, benzoate CH), 7.28(br m, 1, NH), 6.11(m, 1, =CH), 5.86(m, 1, =CH), 5.81 (br m, 1, OH), 5.39(m, 1, NCH), 3.45(d, J=6.0 Hz, 2, OCH$_2$), 3.04(br m, 1,CH of cyclopropyl), 2.87(br m, 1, CH), 2.65–2.55(m, 1, CH), 1.63–1.53(m, 1, CH), 0.70–0.54(m, 4, 2×CH$_2$ of cyclopropyl).

EXAMPLE 11

Preparation of (1S,4R)-cis-4-[2-amino-6-(cyclopropylamino)-9H-purin-9-yl]-2-cyclopentene-1-methanol hemisulfate salt A suspension of (1S,4R)-cis-4-[2-amino-6-(cyclopropylamino)-9H-purin-9-yl]-2-cyclopentene-1-methanol benzoate salt (5 g) in IPA (25 ml) was warmed to 60 to 65° C. A solution of concentrated sulfuric acid (0.64 g) in water (1.25 ml) was added and the resultant cloudy suspension was warmed to 70 to 75° C. The mixture was cooled to 20 to 25° C. and filtered. The solid was washed with IPA (2×10 ml) and dried in vacuo at 40 to 45° C. to give the title compound as a white solid (3.57 g, 87%), spectra identical to those of the product of Example 5.

EXAMPLE 12

Preparation of (1S,4R)-cis-4-[2-amino-6-(cyclopropylamino)-9H-purin-9-yl]-2-cyclopentene-1-methanol glutarate salt (1S,4R)-cis-4-[2-amino-6-chloro-9H-purin-9-yl]-2-cyclopentene-1-methanol hydrochloride salt (EP0434450) (80 g) was heated under reflux in IMS (800 ml) with cyclopropylamine (108 ml) for about 3.5 h. The solution was cooled to 45 to 50° C. and treated with charcoal (8 g) and filter-aid Harborlite J2 (4 g). After about 1 h, the mixture was cooled to 20 to 25° C. and filtered. The solids were washed with IMS (2×160 ml) and the combined filtrates and washings were concentrated by distillation under reduced pressure to about 240 ml. The mixture was diluted with IMS (560 ml) and re-concentrated to about 240 ml. The process of dilution and re-concentration was repeated twice more. The final concentrate was divided into four equal portions. One portion was heated to 70 to 75° C. to give a solution. To this was added a solution of glutaric acid (8.75 g) in water (144 ml) which had been pre-heated to 70 to 75° C. The mixture was cooled to 60 to 65° C. and seeded with authentic (1S,4R)-cis-4-[2-amino-6-(cyclopropylamino)-9H-purin-9-yl]-2-cyclopentene-1-methanol glutarate salt. The mixture was cooled to 0 to 5° C. and filtered. The product was washed with a mixture of water and IMS (4:1, 2×36 ml) and dried in vacuo at 40 to 45° C. to furnish the title compound as a light brown solid (19.9 g, 80%); mp. 184–188° C.; $^1$H-NMR (DMSO-d$_6$) δ: 7.60(s, 1, purine CH), 7.27(br m, 1, NH), 6.10(m, 1, =CH), 5.86(m, 1, =CH), 5.82(br m, 1, OH), 5.39(m, 1, NCH), 3.44(d, J=5.9 Hz, 2, OCH2), 3.04(br m, 1, CH of cyclopropyl), 2.87(br m, 1, CH), 2.65–2.55(m, 1, CH), 2.24(t, J=7.2 Hz, 4, glutarate 2×CH$_2$), 1.70(m, J=7.2 Hz, 2, glutarate CH$_2$), 1.62–1.54(m, 1, CH), 0.68–0.54(m, 4, 2×CH$_2$ of cyclopropyl).

EXAMPLE 13

Preparation of (1S,4R)-cis-4-[2-amino-6-(cyclopropylamino)-9H-purin-9-yl]-2-cyclopentene-1-methanol hemisulfate salt A suspension of (1S,4R)-cis-4-[2-amino-6-(cyclopropylamino)-9H-purin-9-yl]-2-cyclopentene-1-methanol glutarate salt (10 g) in IPA (50 ml) was heated to 60 to 65° C. and a solution of concentrated sulfuric acid (1.18 g) in water (2.5 ml) was added. The resultant suspension was warmed further to 70 to 75° C. and then cooled to 20 to 25° C. The product was filtered, washed with IPA (2×20 ml) and dried in vacuo at 40 to 45° C. to give the title compound as a light brown solid (6.78 g, 85%), spectra identical to those of the product of Example 5.

EXAMPLE 14

Preparation of (1S,4R)-cis-4-[2-amino-6-(cyclopropylamino)-9H-purin-9-yl]-2-cyclopentene-1-methanol hemisulfate salt from the succinate salt in the presence of its enantiomer A mixture of (1S,4R)-cis-4-[2-amino-6-(cyclopropylamino)-9H-purin-9-yl]-2-cyclopentene-1-methanol, succinate salt and its enantiomer (134 g) having an enantiomeric ratio of 97.5:2.5 as shown by chiral HPLC (eluant (1.0 v/v acetonitrile in aqueous 0.05M potassium phosphate buffer, pH 6.5; column ChromTech Chiral-AGP, 100×4.0 mm; flow 1.0 ml/min;detection at 220 nm) was suspended in isopropanol (IPA) (302 ml) and water (67 ml) and heated to reflux to give a clear solution. The solution was cooled to 75 to 80° C. and a solution of concentrated sulfuric acid (16.26 g) in water (33.5 ml) was added, and the solution was clarified by a hot filtration, following through the filter with a mixture of IPA and water (3:1, 134 ml). The filtrates and washings were cooled to 45 to 50° C. and seeded with authentic(1S,4R)-cis-4-[2-amino-6-(cyclopropylamino)-9H-purin-9-yl]-2-cyclopentene-1-methanol, hemisulfate salt. Further IPA (804 ml) was added in this temperature range and the resultant suspension was cooled to 0 to 5° C. The suspension was filtered and the product was washed with IPA (2×200 ml) and dried in vacuo at 40 to 45° C. to give the title compound as a white crystalline solid (75 g, 68%).

Analysis of the product by chiral HPLC (conditions as above) showed the ratio of enantiomers to be 99.2:0.8.

A range of similar experiments was carried out on 8 g scale using different ratios of enantiomers of the input succinate salt with the same experimental protocol. The results are summarised below in tabular form:

| RATIO OF ENANTIOMERS OF INPUT SUCCINATE SALT | RATIO OF ENANTIOMERS OF PRODUCT HEMISULFATE SALT |
| --- | --- |
| 99.5:0.5 | 99.87:0.1 |
| 99.0:1.0 | 99.72:0.3 |
| 98.0:2.0 | 99.47:0.5 |
| 96.0:4.0 | 98.97:1.0 |

EXAMPLE 15

Preparation of (1S,4R)-cis-4-[2-amino-6-(cyclopropylamino)-9H-purin-9-yl]-2-cyclopentene-1-methanol hemisulfate salt from the glutarate salt in the presence of its enantiomer A mixture of (1S,4R)-cis-4-[2-amino-6-(cyclopropylamino)-9H-purin-9-yl]-2-cyclopentene-1-methanol, glutarate salt and its enantiomer (100 g) having an enantiomeric ratio of 98.6:1.4 as shown by chiral HPLC (conditions as above in Example 14) was suspended in isopropanol (IPA) (400 ml) and water (100 ml) and heated to reflux to give a clear solution. The solution was cooled to 70 to 75° C. and a solution of concentrated sulfuric acid (12.01 g) in water (25 ml) was added, followed by a mixture of IPA and water (4:1, 100 ml) and then by IPA (100 ml). The solution was cooled to 50 to 55° C. and seeded with authentic (1S,4R)-cis-4-[2-amino-6-(cyclopropylamino)-9H-purin-9-yl]-2-cyclopentene-1-methanol, hemisulfate salt. Further IPA (800 ml) was added in this temperature range and the resultant suspension was cooled to 0 to 5° C. The suspension was filtered and the product was washed with IPA (2×200 ml) and dried in vacuo at 40 to 45° C. to give the title compound as a white crystalline solid (72 g, 90%).

Analysis of the product by chiral HPLC (conditions as above in Example 14) showed the ratio of enantiomers to be 99.6:0.4.

The application of which this description and claims form part may be used as a basis for priority in respect of any subsequent application. The claims of such subsequent application may be directed to any feature or combination of features described herein. They may take the form of product, composition, process or use claims and may include, by way of example and without limitation, one or more of the following claims.

What is claimed is:

1. A pharmaceutical composition for oral administration comprising (1S,4R)-cis-4-[(2-amino-6-cyclopropylamino)-9H-purin-9-yl]-2-cyclopentene-1-methanol, or a pharmaceutically acceptable derivative thereof, together with citrate and at least one sweetener selected from sorbitol and saccharin, at a pH range of 2.0 to 4.5.

2. A pharmaceutical composition for oral administration comprising (1S,4R)-cis-4-[(2-amino-6-cyclopropylamino)-9H-purin-9-yl]-2-cyclopentene-1-methanol, or a pharmaceutically acceptable derivative thereof, together with citrate and at least one sweetener selected from sorbitol and saccharin, at a pH range of 6.6 to 7.5.

3. A pharmaceutical composition as claimed in claim 1 wherein the sweetener is saccharin and the composition further comprises fructose and acesulfame.

4. A pharmaceutical composition as claimed in claim 2 wherein the sweetener is saccharin and the composition further comprises fructose and acesulfame.

5. A pharmaceutical composition as claimed in claim 1 wherein the pharmaceutically acceptable derivative of (1S,4R)-cis-4-[(2-amino-6-cyclopropylamino)-9H-purin-9-yl]-2-cyclopentene-1-methanol is the hemisulfate salt.

6. A process for formulating (1S,4R)-cis-4-[(2-amino-6-cyclopropylamino)-9H-purin-9-yl]-2-cyclopentene-1-methanol for oral administration comprising the step of bringing (1S,4R)-cis-4-[(2-amino-6-cyclopropylamino)-9H-purin-9-yl]-2-cyclopentene-1-methanol, or a pharmaceutically acceptable derivative thereof, into association with citrate and a sweetening agent which does not contain a carboxyl group.

7. A process as claimed in claim 6 wherein the (1S,4R)-cis-4-[(2-amino-6-cyclopropylamino)-9H-purin-9-yl]-2-cyclopentene-1-methanol is in the form of its hemisulfate salt.

8. A pharmaceutical composition for oral administration comprising (1S,4R)-cis-4-[2-amino-6-cyclopropylamino)-9H-purin-9-yl]-2-cyclopentene-1-methanol, or a pharmaceutically acceptable derivative thereof, citrate, and a sweetening agent compatible with said (1S,4R)-cis-4-[2-amino-6-cyclopropylamino)-9H-purin-9-yl]-2-cyclopentene-1-methanol, or pharmaceutically acceptable derivative thereof.

9. A pharmaceutical composition as claimed in claim 8 at a pH range of 2.0 to 4.5.

10. A pharmaceutical composition according to claim 9 wherein the pH range is 3.8.

11. A pharmaceutical composition according to claim 10 wherein the pH is 4.1.

12. A pharmaceutical composition as claimed in claim 8 wherein the sweetening agent is selected from the group consisting of sorbitol, saccharin, acesulfame, fructose, sucralose, and aspartame.

13. A pharmaceutical composition according to claim 8 wherein the citrate ion concentration is in the range of 0.01 M to 0.1 M.

14. A pharmaceutical composition according to claim 1 in the form of a solution.

* * * * *